United States Patent [19]

Studer, Jr.

[11] 4,090,920
[45] May 23, 1978

[54] DISPOSABLE ANTIBIOTIC SUSCEPTABILITY TEST PACKAGE

[75] Inventor: John Eugene Studer, Jr., Flemington, N.J.

[73] Assignee: Fisher Scientific Company, Pittsburgh, Pa.

[21] Appl. No.: 779,413

[22] Filed: Mar. 18, 1977

Related U.S. Application Data

[63] Continuation of Ser. No. 659,452, Feb. 19, 1976, abandoned.

[51] Int. Cl.$^2$ ............................ C12K 1/04; C12K 1/10
[52] U.S. Cl. ...................................... 195/127; 195/140; 195/103.5 K
[58] Field of Search ................ 195/103.5 R, 127, 139, 195/103.5 K, 103.5 M, 140

[56] References Cited

U.S. PATENT DOCUMENTS

| | | | |
|---|---|---|---|
| 3,597,326 | 8/1971 | Liner | 195/139 |
| 3,713,985 | 1/1973 | Astle | 195/127 X |
| 3,826,717 | 7/1974 | Gilbert et al. | 195/139 X |

Primary Examiner—Alvin E. Tanenholtz
Assistant Examiner—Robert J. Warden
Attorney, Agent, or Firm—Webb, Burden, Robinson & Webb

[57] ABSTRACT

The susceptibility of microorganisms to various antibiotics is determined by propagating microorganisms in the presence of different concentrations of the antibiotic in a plurality of test wells or chambers, in a culture test plate which has a row of rectangular wells for photomechanical optical reading. The test plate is disposable of one piece plastic, with a separate protective cover, and readily moldable. A series of concentrations of a particular antibiotic are prepackaged and stored dry in the test wells of a single test plate. Various antibiotics in test plates may be stacked for convenience in handling and incubation.

4 Claims, 13 Drawing Figures

U.S.Patent May 23, 1978 Sheet 1 of 2 4,090,920

DISPOSABLE ANTIBIOTIC SUSCEPTABILITY TEST PACKAGE

This is a continuation, of application Ser. No. 659,452, filed Feb. 19, 1976, now abandoned.

BACKGROUND OF THE INVENTION

This invention relates to antibiotic susceptibility testing and more particularly a test assembly of a series of rectangular wells in which wells are placed various concentrations of various antibiotics or therapeutic control agents to ascertain the interaction between such control agents and various microorganisms, usually pathogenic. With the proliferation of antibiotics and other drugs both in the hospital and in the laboratory as well as educational insitutions there is an increasing demand for information concerning the susceptibility or sensitivity of a particular microorganism to various antibiotics or drugs, as well as information on the assay of particular constituents in blood, or other biological liquids.

PRIOR ART

The use of automated analytical procedures has become of increasing importance. For both chemical and biological procedures the number of samples to be run has been increasing exponentially as new procedures are developed, and existing procedures are adapted to large quantity requirements.

U.S. Pat. No. 3,272,719 - METHOD AND APPARATUS FOR DETERMINING THE SENSITIVITY OF BODY FLUID INFECTANTS TO DRUGS, Avakian, Sept. 13, 1966 shows rectangular or square compartments, with a common wall between adjacent rows and files. A notch is provided for a string saturated with infected fluid to sag into compartments containing a sterile nutrient and known concentrations of drugs under test.

U.S. Pat. No. 3,301,065 — LIQUID SAMPLE SUPPLY APPARATUS, Fahrenbach, Bell and Sandage, Jan. 31, 1967, shows an automatic sampling system in which a series of cups containing samples are fed serially into an analytical system. The samples may be in cups on a spiral in a plate, or may be fed as a series of individual pallets locked together and fed along a belt. Locking the pallets together insures coordination in feeding separate pallets.

Belgium Pat. No. 691,532, Feb. 28, 1967, shows lyophilized antibiotics or chemotherapeutic agents in various concentrations, including a blank, in separate cells arranged in columns and rows in a tray, for testing the resistance of microorganisms to antibiotics or agents. Retaining appendices project from the base of the culture cells to retain the lyophilized material in the individual cells. Identifying covers cooperate with each cell close, and identify the contents of, each cell. A culture medium and/or indicator may be present in the lyophilized state in the test cells. The cells and the covers are essentially transparent to permit observation of the cultures.

U.S. Pat. No. 3,649,464 - ASSAY AND CULTURE TRAY, Freeman, Mar. 14, 1972, shows a transparent tray having rows and columns of upstanding cups or wells, which are spaced apart to avoid cross-contamination. A peripheral wall around the tray permits stacking of a set of trays. A strip having a series of well seals is shown to seal off an individual row of wells.

U.S. Pat. No. 3,713,985 — DEVICE AND METHOD FOR TESTING POTENCY OF BIOLOGICAL CONTROL REAGENTS, Astle, Jan. 30, 1973, shows a series of biological reagents in a series of cups, in a strip, or pallet, with the strips having dovetails to longitudinally lock a group of the strips together to form a tray. A foil cover to protect lyophilized contents during storage is disclosed, with reconstitution of the contents at time of use. The culture medium and the test organism are added sequentially and separately at time of use, so that the control reagent is first redispersed. It is then inoculated, and incubated.

U.S. Pat. No. 3,890,201 — MULTI-CHAMBER IMPEDANCE MEASURING MODULE-CAP COMBINATION, Cady, June 17, 1975, shows rows and columns of upstanding cylinders on a flat base, forming cells, with electrically conductive strips in each cell to permit impedance measurement of the cell contents. The impedance in the cell is a function of microorganism growth. Separate caps are provided for each cell to permit gas flow into the individual cells during incubation.

SUMMARY OF THE INVENTION

It has now been found that the susceptibility of various microorganisms to antibiotics can be particularly conveniently determined by using a biological culture test plate which is a molded transparent plate of a biologically inert plastic such as a polymer of methyl methacrylate, or a vinyl resin, but which may be of any biologically inert transparent or nearly transparent plastic, which plate has a row of approximately rectangular wells. The wells preferably have a slight taper, which permits molding in simplified molds. By having about $\frac{1}{2}°$ to 4° draft or molding taper on all vertical surfaces, a two piece mold can be used to economically produce the test plates. A slight taper permits the use of a mechanical light source, and optical reader or scanner, with negligible inaccuracies from the taper. Parallel sides which are more optically true can be used, and while optically more desirable, increase the cost of production of the test plates. Visual inspection or "eyeball" reading is often used to detect inhibition of growth in the several wells.

For incubation a well cover protects from chance contamination. A flexible plastic such as polyethylene is low in cost, and readily molded. The well cover is shaped to fit an entire plate row of wells, often 8 or 10, and has a rim to fit into each well, thus closing the well and positioning the well cover. A lifting flap on the well cover permits the well cover to be readily lifted from the test plate. The well cover is reversible, so that in one position the lifting flap is flat against the test plate, and when rotated 180°, extends outwardly as an indexing flap. The flap may be treated to improve the adhesion of an ink or label.

By having a number of test plates with wells in each, a separate antibiotic can be used in each test plate. Different patients in a hospital may have different spectra of antibiotics to be tested.

By being stackable, a stack of 5 or 10 can be handled as a unit in incubation and storage. A plurality of test plates, 5 or 10, are conveniently stacked with a dehydrating agent in a bag until time of use. A foil bag may be used to give maximum moisture protection from moisture.

DRAWINGS

Other advantages and objects will be obvious from a more detailed description of the device as shown in the accompanying drawings in which.

Figure 2:
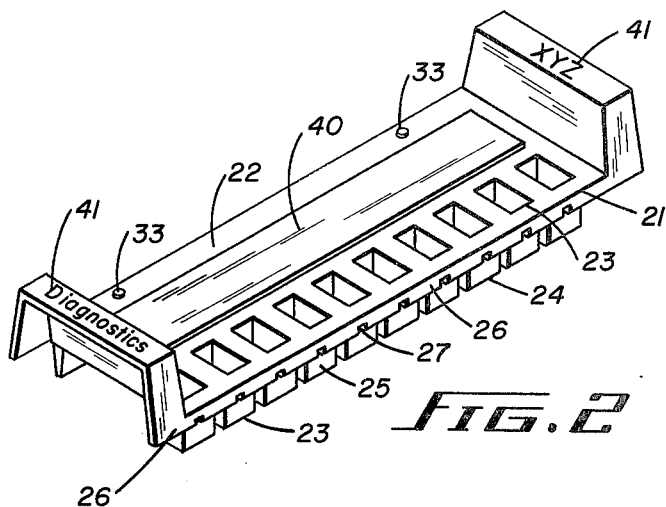
FIG. 2 is a pictorial view of a single culture test plate.

As shown in FIG. 2 the biological culture test plate 21 consists of a flat platform 22 having therein a series of rectangular wells 23. Each rectangular well has a flat bottom 24 and approximately rectangular walls 25. By using approximately parallel walls, light can be passed through two approximately parallel walls with minimum distortion or bending; which permits either inspection by eye or a mechanical optical device to measure the turbidity of materials within the well. It is desirable that the well have a slight taper within the range of about ½° to 4° as such taper permits the molding of wells, and the withdrawal of the molding mandrel. If there is no taper, it is more difficult to withdraw the mandrel; and if the taper is more than about 4° the well starts to become somewhat prismatic in its action on light.

As shown in FIG. 2 for the specific embodiment shown, there is a series of 10 wells. Obviously, the number of wells may vary but 10 is a convenient number for most test purposes.

At the front of the flat platform 22 is a dependent or downwardly extending front skirt 26. The front skirt gives additional rigidity, and also has therein a group of indexing notches 27. Each indexing notch is in a coordinated spacial relationship with a well. Conveniently the notches are centered with respect to each well and serve the purpose of indexing the test plate with respect to a reading device when a mechanical feed system is used in connection with an electrooptical density reading system.

Conveniently, but not necessarily, at the back of the flat platform is a rear skirt 28. Also adjacent the rear of the platform is a stiffening rib 29. This rib is slightly tapered for convenience in molding and extends downwardly from the flat platform a sufficient distance that the test plate rests horizontally on a horizontal flat surface. Preferably, the stiffening rib and the wells have a common bottom plane. This provides for the culture test plates to rest flat on a work surface during filling and culturing, and also that permits the test plates to be stacked without tipping.

In the ends of the test plate are stacking handles 30. These handles are interiorly hollow and tapered whereby the handles nest when test plates are stacked. The front and rear of the handles conveniently are extensions of the front skirt and rear skirt 26 and 28 and have a rise member 31 and a flat top 32 on each end. The skirt extensions are at such an angle that when stacked, the assembly nests without binding but without undue free motion.

The top of the flat platform above the stiffening rib may have spacing buttons 33. These spacing buttons 33 are such size that when well snap covers 34, referred to below, are placed in the wells the stiffening rib contacts the spacing buttons and gives uniform vertical stacking.

For shipment, incubation, and storage, the wells are closed and the contents protected by a well snap cover 34. The well snap cover is of a thin sheet 35 of flexible plastic. It is slightly larger than the wells to be covered and has depending therefrom a series of rectangular well seals 36.

Figure 7:
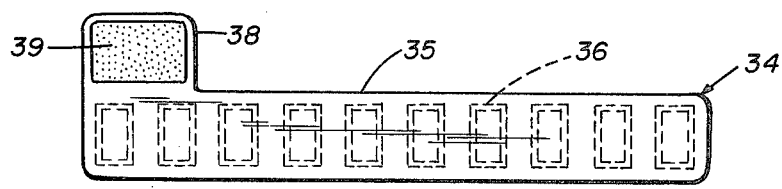
FIG. 7 is a view of a plastic snap cover.
Figure 10:
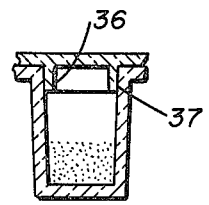
FIG. 10 shows a sectional view of the well with the snap cover in place.

As shown in FIG. 7 and 10 each well seal has a rectangular configuration and such size as to fit into a rectangular well 23. The spacing between them corresponds to the spacing in the series of rectangular wells 23. The well seals are conveniently hollow and extend part way into the well in assembled position. The rims 37 conveniently are a easy press fit into the rectangular well 13 so that the snap cover 34 may be easily removed and replaced, and when placed in position will not fall out under shipping and handling stresses. Also on the snap cover is a lifting flap 38. The lifting flap has in part a textured area 39. The textured area is formed in molding by texturizing the mold so that the texturized area is roughened and accepts ink or a label more readily than the smooth surface of the snap cover. The lifting flap conveniently extends from the snap cover about the width of the snap cover and when placed inwardly fits against the cultured test plate so that the lifting flap 38 can be picked up with a fingernail; but can be rotated 180° upon a vertical axis so that the lifting flap extends outwardly as an identification tab.

The textured area on the lifting flap of the snap cover permits the identification of a particular culture test plate in a stack. Conveniently but not necessarily, on the face of the culture test plate 21 is a label 40. Conveniently the label includes the name of the antibiotic or active agent, identification as to batch number, dates and origin and has room for the name of the patient, the date of the test and other information at the time of use.

The ends of the handles 30 may have a molded legend 41 therein. It is convenient for a trademark or name of the manufacturer to be molded into the surface of the handle for identification.

Figure 8:
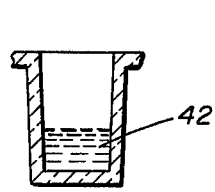
FIG. 8 is a sectional view of a well filled with liquid.

The use of the culture test plate is shown in FIGS. 8 through 13. The culture test plate is molded with 10 rectangular wells. As shown in FIG. 8 the well is filled with a liquid antibiotic solution 42 which has an appropriate binder. poly(vinyl pyrrolidone) makes an excellent binder in that it is biologically inert and has no effect on the antibiotic, the culture medium or the microorganisms; and yet when frozen and dried, fills the well with a sponge which resembles cotton candy in texture which holds the antibiotic in place and prevents migration of the antibiotic.

Figure 5:
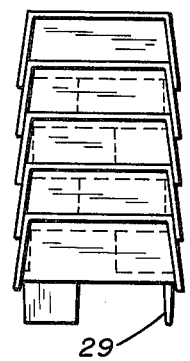
FIG. 5 is an end view of a stack of 5 culture test plates stacked for shipment or handling.
Figure 3:
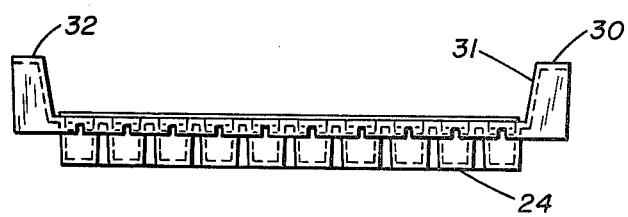
FIG. 3 is a side elevation of a single culture test plate.
Figure 4:
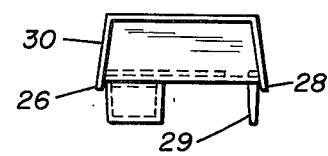
FIG. 4 is an end view of a culture test plate.
Figure 6:
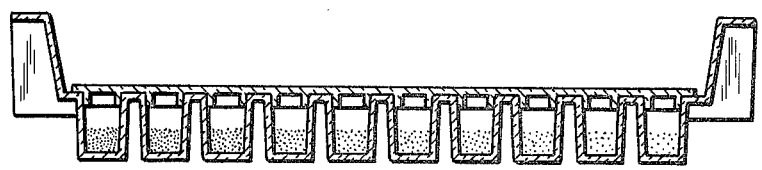
FIG. 6 is a sectional view of a culture test plate with a plastic snap cover closing the individual wells.
Figure 9:
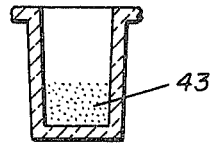
FIG. 9 is a sectional view of the well after the liquid has been frozen and dried.

As shown in FIG. 9 the liquid filled into the wells is frozen and dried to form a dried antibiotic in the binder 43. Conveniently, a group of the culture test plates are stacked with the well snap covers removed, as for example as shown in FIG. 5, and a group of such stacks are placed on the shelves of a freezing chamber, the contents frozen, the chamber evacuated and using conventional lyophilizing techniques dried to a sponge. The dryness of the sponge is protected by replacing the well snap covers and storing in a dry environment until time for use.

FIG. 10 shows the dried sponge with the well snap cover in position.

Figure 11:
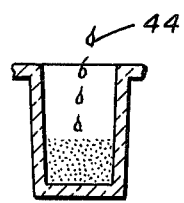
FIG. 11 shows the contents of a well being reconstituted by the addition of a liquid.

At time of use, as shown in FIG. 11, a liquid diluent is added to the dry sponge.

Usually, using tube dilution practice, the liquid diluent is an appropriate culture medium 44 which has been inoculated with a test organism. Preferably the test organism is at a standard concentration so that the test plate results are quantitative as well as qualitative.

Theoretically, the culture medium itself may be mixed with the antibiotic and dried down and retained in storage so that only the test organism and in an inert diluent, namely water, need be added at the time of use. It is preferred that the culture medium be added with the test organism (1) because the test organism can be added to the culture medium before it is added, to avoid a double addition, (2) a culture medium can be chosen which is particularly appropriate for a specific test organism, and (3) the test organism concentration is uniform for all tests. Different laboratories prefer different culture media for different organisms or even the same organism. By adding the organism being tested in the culture medium there is additional flexibility in selecting the culture medium. Also, without the culture medium, there is a minimum risk of having a system present which could support bacterial growth during storage.

Figure 12:
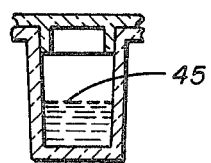
FIG. 12 shows a view in section of a well with the snap cover in place, showing the clear liquid either before the growth of any microorganisms or with the growth having been inhibited.
Figure 13:
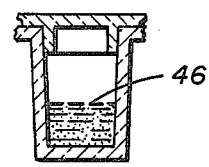
FIG. 13 shows a single well with the snap cover in place with a cloudy or turbid liquid resulting from the propagation of microorganisms therein.

In FIG. 12 is shown a well having a clear solution 45 therein. After the sponge and antibiotic have dissolved in the culture medium, the solution is clear. If there is sufficient antibiotic to inhibit growth of the test organism, the solution remains clear, if not, the microorganism grows and causes the solution to become cloudy 46 as shown in FIG. 15.

A clear solution 45 shows no bacterial growth. The cloudy solution 46 shows bacterial growth.

The reading of the solutions to determine bacterial growth may be either by inspection with the human eye, in effect an "eyeball" reading, or it may be done by electrooptical equipment such as a photosensitive reader and a constant intensity light. The light may have a selected wave length or color depending upon the solution. Separate readers may be used for each cell or the same reader may be used for a group of 10 cells in a culture test plate serially.

Figure 1:
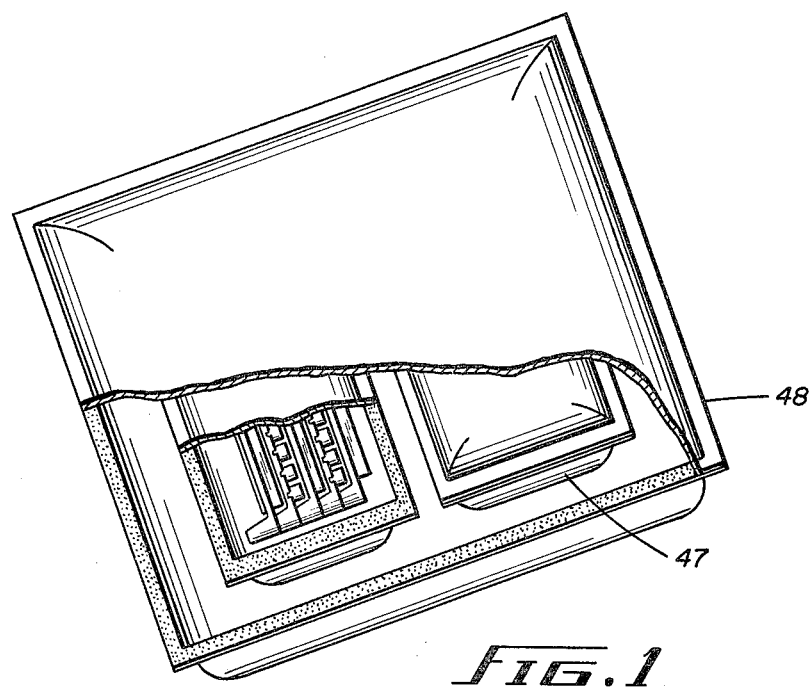
FIG. 1 is a pictorial view showing a group of test plates in each of two plastic bags which are sealed inside of a moisture proof foil envelope.

For shipment and storage a group of 5 test plates in a stack are conveniently enclosed in a plastic envelope 47 as shown in FIG. 1. A dessicant may also be placed in the envelope to insure dryness. Two or more such plastic envelopes may then be placed in a foil outer envelope 48. The foil outer envelope may have additional dessicant envelopes in it and is sealed so as to protect its contents from ambient moisture for an extended length of time.

When so sealed, the present culture test plates maintain essentially their original labeled potency for several months, and it can be expected that the test plates will be satisfactory for at least several years.

The size of the wells is not critical but a well size of 8 × 10 mm. with 10 mm. depth permits working with 0.4 ml. of fluid with the wells half full, and permits a convenient working size with the consumption of a minimum quantity of reagents and materials. A thickness of the cells themselves, the test plate, and the handles through out, of about 0.8 mm. (1/32 inch) gives good results. Such a thickness is a compromise between having the parts thick enough for strength and thin enough to require a minimum of materials. With such a thickness the culture test plates are strong enough to be reused if desired but are sufficiently inexpensive that it is usually cheaper to consider the test plates as disposable.

Without being limited thereto a typical usage of the present culture test plate is shown in the following example:

EXAMPLE

Culture test plates are for use in the quantitative determination of the susceptibility in vitro of bacteria to antimicrobial agents. The test permits the determination of the minimal concentration of an agent needed to inhibit or to kill a microorganism.

The basis of the culture test plate method is the broth or tube dilution technique. Details of standardized methods and recommendations for use of this procedure are found in (1) Ericson, H. M. and Sherris, J. C., "Antibiotic Sensitivity Testing, Report of an International Collaborative Study," *Acta Path. Microbiol. Scand. Sect. B, Suppl.* 217 (1971); and (2) Manual of Clinical Microbiology, Second Edition, Lennette, E. H., Spaulding, E. H., and Truant, J. P., Eds. American Society for Microbiology (1974).

The antibiotic to be tested is provided in the two-fold dilution range of interest by starting with 10 four liter flasks into the first of which was added 6 g. of poly(vinyl pyrrolidone) (Povidone USP) and 3 liters of triple distilled water. In each of the other nine flasks was added 3 g. of poly(vinyl pyrrolidone) and 1,500 ml. of triple distilled water.

To the first flask was added 206.25 mg. of tetracycline hydrochloride, after which the flask was shaken until the contents were dissolved and uniformly distributed. One half of the contents of the first flask was then added to the second flask and the contents of the second flask shaken until uniform. One half of the contents of the second flask was then added to the third flask, etc., and the series continued until the serial two-fold dilution was obtained in the ninth flask. The excess diluted solution in the ninth flask was discarded. The tenth flask had only poly(vinyl pyrrolidone) and triple distilled water. It may be left empty.

The contents of each flask were sterilely filtered into two liter reagent bottles which were capped and kept in an ice-water bath for filling by sterile techniques. Filling should not be unduly delayed. The solutions normally remain stable and without change for at least 24 hours if kept cold, but it is preferable that they be filled immediately to guarantee against loss of potency.

2/10 ml. of the contents of each of the flasks were filled into the respective wells of a single test plate.

The wells in a total of five thousand test plates were filled, the test plates stacked and placed in racks in a cold chamber. The cold chamber was pre-chilled with the cold chamber being maintained at colder than −40° C with shelf cooling being maintained until the contents of all of the wells in all of the test plates were frozen solid. This should occur in less than 12 hours. After freezing, the cold chamber was evacuated to less than 100 microns total pressure, after which the shelf temperature was raised to about 10° C and maintained at this temperature until temperature probes in the assembly indicate that the temperature within the wells was within about 5°–10° C of the temperature of the shelves themselves. The shelves were then warmed up to about 30° C, and after the test plates had warmed up appropriately, the temperature was increased to 40° C and the chamber held for 4 hours. At this point the contents of each well was thoroughly dry.

While continuing the use of sterile techniques, well snap covers were placed over the dried test plate wells and a set of 5 test plates were stacked for convenience and placed in a polyethylene plastic envelope. A 5 g. silica gel packet was placed in each of the plastic envelopes to aid in maintaining dryness. Two such envelopes containing 5 test plates each were then placed in an outer foil pouch which foil outer envelope is essentially impermeable to moisture and maintains dryness of the test plates for an extended period of at least months and predictably for at least several years, if not indefinitely.

Conveniently but not necessarily, the culture test plates have a label on each which indicates the particular antibiotic and its concentration in each of the wells with, space for identification data as to the patient and test conditions under which the culture test plate is used. A number of foil envelopes are packaged in a shipping container, the number being based on the usage of customers.

When filled in this fashion, the wells contain:

TABLE

| Well No. | | | |
|---|---|---|---|
| 1 | $12.5\gamma$ | tetracycline hydrochloride + 10% excess plus 400 Povidone | |
| 2 | $6.25\gamma$ | " | " |
| 3 | $3.125\gamma$ | " | " |
| 4 | $1.56\gamma$ | " | " |
| 5 | $0.78\gamma$ | " | " |
| 6 | $0.39\gamma$ | " | " |
| 7 | $0.195\gamma$ | " | " |
| 8 | $0.098\gamma$ | " | " |
| 9 | $0.049\gamma$ | " | " |
| 10 | $0.00\gamma$ | — | " |

Culture test plates conveniently are used for any antibiotic or therapeutic control agent such as penicillin, ampicillin, clindamycin, erythromycin, methicillin, tetracycline, minocycline, cephalothin, gentamycin, colistin, carbenicillin, chloramphenicol, kanamycin and any of the sulfonamides.

Other antibiotics, either those known or those yet to be discovered may be used—and if the antibiotics require a range other than that listed, the concentration may be modified—but with the wide range covered by the nine dilutions in the cavities, the proper dosage of most antibiotics will be obtained.

The tenth cup has no antibiotic and hence if inoculated with the test microorganism, shows the growth of the microorganism under uninhibited conditions; or if not inoculated is used to show that no contaminants are present.

The number of culture test plates and choice of culture test plates, each with a different antibiotic, depends upon the preferences of the medical staff of the using facility.

At the time of use, aliquots of broth inoculated with the bacterial culture to be tested are pipetted into each plate well following which the plates are incubated for a specified time at an indicated temperature. The test is read by visual inspection for growth as indicated by turbidity or no growth as shown by a non-turbid suspension. The endpoint is defined as the well containing the lowest concentration of antibiotic with no detectable microbial growth. The control well on each plate, having no antimicrobial agent present, serves as a measure of the uninhibited growth of the bacterial culture.

PROCEDURE

Specimens obtained in the laboratory from clinical sources are cultured on primary agar plates. Isolated colonies of the organism suspected of being implicated in an infectious process should be selected.

Ideally, identification procedures should be performed concurrently with susceptibility testing.

Mixtures of different types of organisms (mixed cultures) should not be used for susceptibility testing unless there is a clinical emergency. In these instances, or in circumstances where testing is done directly from clinical specimens, susceptibility tests should be repeated using a pure culture.

Aerobic, facultatively aerobic and clinically significant obligative anaerobic bacteria may be used for susceptibility testing. Anaerobic bacteria should be suspended in freshly boiled medium, dispensed into plate wells and incubated under anaerobic conditions within 15 minutes.

Three to five colonies of the organism to be tested are suspended in 4 to 5 ml. of sterile trypticase soy broth. The tube containing this inoculum is covered and placed in a water bath for incubation at 34°–36° C for two or three hours or until a turbid suspension is produced.

The bacterial density of the inoculum is preferably standardized at $1 \times 10^5$ Colony Forming Units (CFU) prior to use.

The required $1 \times 10^5$ CFU/ml suspension of bacteria can be standarized by preferably adjusting to $10^5$ CFU/ml with the use of a standardized nephelometer.

Altneratively a $BaSO_4$ standard as used for the Kirby-Bauer disc diffusion test can be employed.

0.5 ml. of 0.084 M $BaCl_2$ or 1.17% (w/v) $BaCl_2.2H_2O$ is added to 99.5 ml. of 0.36% (1% v/v) $H_2SO_4$. This suspension is equivalent to approximately $10^8$ Enterobacteriaceae per ml.

The $BaSO_4$ turbidity standard should be dispensed into tubes of the same size used to grow the broth inoculum and stored in the dark for no longer than six months at 20°–25° C. These turbidity standards must be vigorously mixed prior to use.

The inoculum, when standardized by visual comparison against the $BaSO_4$ turbidity standard ($10^8$ CFU/ml), should be then diluted 1:1000 by mixing 0.1 ml. of the bacterial suspension with 99.9 ml. of fresh sterile broth. The diluted suspension now contains $10^5$ CFU/ml.

Broth media used for dilution of the initial bacterial suspension is Mueller-Hinton broth, except when testing with organisms such as streptococci, neisseria, hemophiline rods, and certain other fastidious organisms. Trypticase soy broth may be used for streptococcal cultures. Supplementation of media for growth of fastidious species should be done according to recommendations of the International Collaborative Study, supra.

The plastic snap covers are removed from each culture test plate and are placed on a clean surface, preferably in an inverted position.

Each well of the plate is then filled with 0.2 ml (200 μl) of broth standardized to contain $10^5$ CFU/ml of the microorganism under test.

A repetitive pipetting device may be used to introduce the inoculated broth into the plate wells providing the delivery at the indicated volume is within ±5% and the device can be sterilized prior to use without affecting the delivery, or a manual pipette may be used.

The plastic covers are then snapped back into place using the same covers originally removed from the plate and the plates put in an incubator at 35°–36° C.

Grossly discernible growth is observed in most instances in four to six hours with rapidly growing bacteria. A Minimum Inhibitory Concentration (MIC) endpoint taken at this time has been shown to be equivalent to endpoints taken after 18 hours of incubation in tests done with microorganisms whose growth is rapid. In addition, tests with bacteria exhibiting a slower rate of growth indicate that preliminary MIC's can be found after four to six hours of incubation although plates should be incubated for the full 18 hours to obtain the final result.

The endpoint is defined as the well containing that concentration of antimicrobial agent where there is no detectable microbial growth estimated visually as confluent turbidity or reasonable amounts of flocculation or clusters of bacteria.

A slight haze or a small number of particles seen at the bottom of the well does not constitute growth.

The MIC in mcg or units per ml. is obtained by multiplying the corresponding content figure imprinted next to the well showing no growth by 5.

In addition to determination of MIC, a Minimum Bactericidal Concentration (MBC) can be determined by removal of a loopful of organisms from two or more wells on either side of the MIC breakpoint, plating them out on a solid medium and observing for viable organisms after an incubation period.

In use in a laboratory or hospital it is customary to have a plurality of test plates such as above described and in which have been placed a group of different antibiotics or chemotherapeutic agents and the various test plates containing antibiotics to be tested are cultured together and read either by visual inspection, a so called "eyeball" test, or by using a radiation source such as an electric light and a suitable radiation detector with the test well placed between the radiation source and the detector. For small operations it is convenient to use a single electro-optical reader. For larger installations a group of 10 so that all ten of the wells in a test plate may be read simultaneously is convenient.

The report of the minimum inhibitory concentration of each antibiotic or chemotherapeutic agent is reported so the attending physician can select an antibiotic which is most effective for a particular patient.

I claim:

1. A biological culture test plate of a biologically inert transparent moldable plastic comprising:
   a flat platform of an inert transparent moldable plastic,
   said platform having therein a single row of separate rectangular wells extending adjacent a front edge of said platform, each well having a separate flat bottom and four separate approximately rectangular walls, the walls of each well having a slight taper to permit ready release from molding dies, and upstanding stack handles on each end of said platform, said handles being interiorly hollow, the platform having a skirt extending downwardly from the front edge thereof, the front edge of the skirt and the front of the handles forming a single plane, the backs of the handles forming a second plane, the planes being tapered so as to telescope whereby a plurality of test plates may be stacked in stable configuration with the handles telescoped and the handles may be used to manipulate a single test plate.

2. The biological culture test plate of claim 1 in which the downwardly extending skirt has an indexing notch therein in coordinate spatial relationship with each well,
   a stiffening and spacing rib parallel to the row of wells, extending, from the said platform, adjacent the rear edge of said platform, downwardly to about the same distance as the external depth of said wells, whereby the bottoms of said wells and said rib lie in a common horizontal plane such that said test plate can rest horizontally on a horizontal flat surface upon which said plate is to be supported and whereby a group of such assemblies stack uniformly.

3. The biological culture test plate of claim 1 in which the flat platform has a label attached on the upper surface thereof for indication of antibiotic activity of the samples in each well, the name of patient and other data.

4. The biological culture test plate of claim 1 having:
   a well snap cover of flexible plastic, a series of rectangular well seals on said cover spaced to fit into and seal each well in a test plate, said seals being shaped to fit partially into each rectangular well, and having a thin downwardly extending rim which is an easy press fit in a well,
   and a lifting flap on said cover, which in a first position fits flat against the flat platform, and in a second position, when rotated 180° about a vertical axis extends outwardly beyond the flat platform, to serve as an identification tab.

* * * * *